United States Patent
Sun

(10) Patent No.: US 9,155,611 B2
(45) Date of Patent: Oct. 13, 2015

(54) BRANCH VESSEL STENT GRAFT

(75) Inventor: Jichao Sun, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1045 days.

(21) Appl. No.: 11/481,763

(22) Filed: Jul. 6, 2006

(65) Prior Publication Data

US 2007/0010874 A1 Jan. 11, 2007

Related U.S. Application Data

(60) Provisional application No. 60/697,174, filed on Jul. 7, 2005.

(51) Int. Cl.
*A61F 2/07* (2013.01)
*A61F 2/06* (2013.01)
*A61F 2/89* (2013.01)

(52) U.S. Cl.
CPC ... *A61F 2/07* (2013.01); *A61F 2/89* (2013.01); *A61F 2002/065* (2013.01); *A61F 2002/067* (2013.01); *A61F 2002/075* (2013.01); *A61F 2220/005* (2013.01); *A61F 2220/0075* (2013.01); *A61F 2230/005* (2013.01); *A61F 2230/0054* (2013.01); *A61F 2230/0067* (2013.01)

(58) Field of Classification Search
CPC ....... A61F 2/07; A61F 2/89; A61F 2002/065; A61F 2002/067; A61F 2002/075; A61F 2/844; A61F 2002/072; A61F 2002/8483; A61F 2230/005; A61F 2250/0007; A61F 2230/0054; A61F 2220/0091; A61F 2/06

USPC ......... 623/1.12–1.13, 1.16, 1.35, 1.32; 604/8; 606/151, 228, 230, 232

See application file for complete search history.

(56) References Cited

U.S. PATENT DOCUMENTS

| 5,755,770 A | * | 5/1998 | Ravenscroft | 623/1.13 |
| 6,045,557 A | | 4/2000 | White et al. | |
| 6,306,164 B1 | * | 10/2001 | Kujawski | 623/1.35 |
| 6,569,191 B1 | * | 5/2003 | Hogan | 623/1.11 |

(Continued)

FOREIGN PATENT DOCUMENTS

| JP | 10-513078 A | 12/1998 |
| JP | 11-512013 A | 10/1999 |

(Continued)

OTHER PUBLICATIONS

International Search Report from Corresponding PCT application Serial No. PCT/US2006/026226.

(Continued)

*Primary Examiner* — Melanie Tyson
*Assistant Examiner* — Sidharth Kapoor
(74) *Attorney, Agent, or Firm* — Brinks Gilson & Lione

(57) ABSTRACT

A stent graft (10) has a tubular body of a biocompatible material and a side arm (20) fastened to the tubular body. A tubular extension piece (24) is sealingly joined to the end of the side arm and extends from it. It can be joined with adhesive or stitching. The extension piece can be formed from an elastomeric biocompatible material such as Thoralon™. The extension piece can have a resilient reinforcement 44 embedded into it and extending longitudinally. The extension piece is tucked back into the side arm during deployment of the stent graft into a body lumen.

4 Claims, 4 Drawing Sheets

(56) References Cited

U.S. PATENT DOCUMENTS

| | | | |
|---|---|---|---|
| 6,712,842 B1* | 3/2004 | Gifford et al. | 623/1.13 |
| 2001/0047198 A1* | 11/2001 | Drasler et al. | 623/1.13 |
| 2002/0065552 A1* | 5/2002 | Jayaraman et al. | 623/1.46 |
| 2002/0099441 A1 | 7/2002 | Dehdashtian | |
| 2003/0088305 A1* | 5/2003 | Van Schie et al. | 623/1.12 |
| 2003/0199967 A1* | 10/2003 | Hartley et al. | 623/1.13 |
| 2004/0082990 A1* | 4/2004 | Hartley | 623/1.13 |
| 2004/0111148 A1* | 6/2004 | Goodson | 623/1.16 |
| 2004/0230287 A1* | 11/2004 | Hartley et al. | 623/1.12 |
| 2005/0080482 A1* | 4/2005 | Bonsignore | 623/1.35 |
| 2005/0131519 A1 | 6/2005 | Hartley | |
| 2005/0177222 A1* | 8/2005 | Mead | 623/1.13 |

FOREIGN PATENT DOCUMENTS

| | | |
|---|---|---|
| JP | 2003-220081 A | 8/2003 |
| WO | WO 97/09007 A1 | 3/1997 |
| WO | WO 2004/017867 A1 | 3/2004 |

OTHER PUBLICATIONS

Examiner's first report for corresponding AU Application No. 2006269444 dated Feb. 28, 2011 (2 pages).

Examiner's report No. 2 for corresponding AU Application No. 2006269444 dated May 10, 2011 (2 pages).

Office Action for corresponding Canadian Application No. 2,613,330 dated Mar. 14, 2013 (2 pages).

Office Action for corresponding EP Application No. 06774523.2-2320 dated May 18, 2011 (3 pages).

Office Action for corresponding EP Application No. 06774523.2-2320 dated Mar. 15, 2012 (4 pages).

Office Action and translation for corresponding JP 2008520366 dated Aug. 9, 2011 (6 pages).

International Preliminary Report on Patentability for corresponding PCT/US2006/026226 dated Jan. 10, 2008 (6 pages).

* cited by examiner

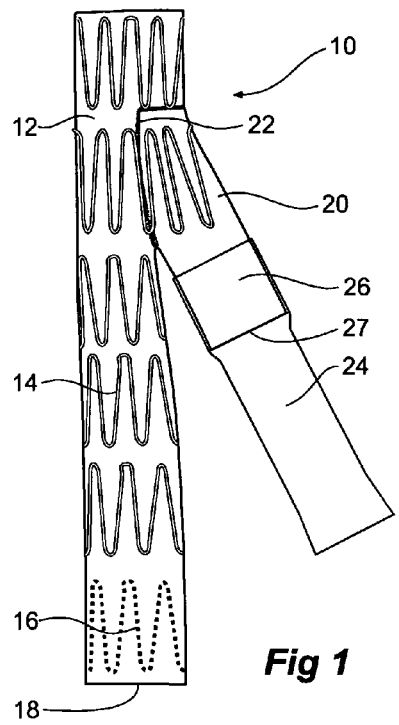
Fig 1
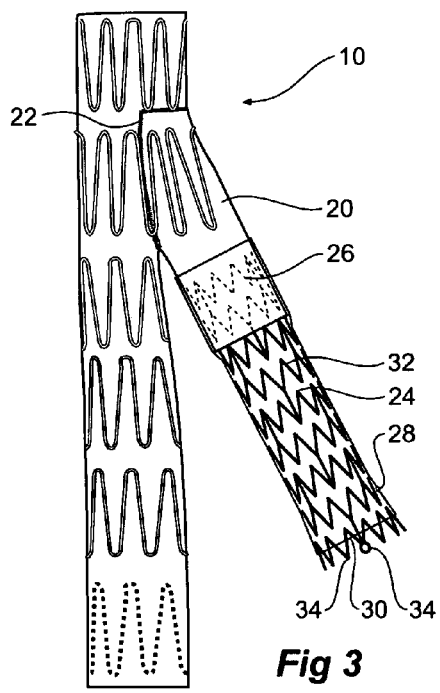
Fig 3
Fig 2
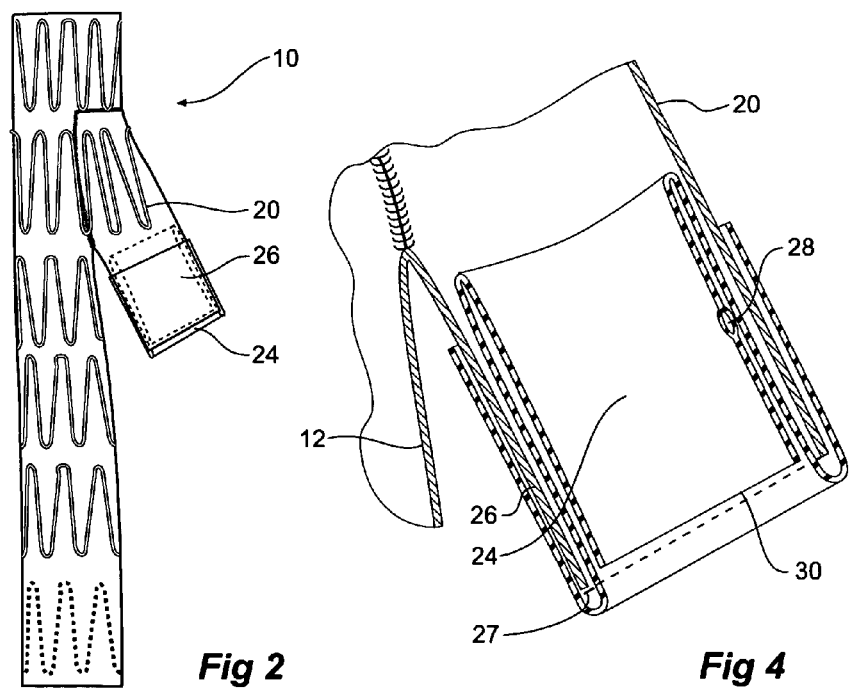
Fig 4

BRANCH VESSEL STENT GRAFT

CROSS-REFERENCE TO RELATED APPLICATIONS

This application claims priority of provisional application Ser. No. 60/697,174, filed Jul. 7, 2005.

TECHNICAL FIELD

This invention relates to a medical device and more particularly to a medical device for endovascular deployment into a body lumen such as the vasculature of an animal or human.

BACKGROUND OF THE INVENTION

It is known to use branch vessel stent grafts deployed into vasculature of a human or animal to provide and alternate flow path where the vasculature has been damaged by accident or disease. The branch vessel stent graft allows an extension piece to be deployed from a main graft into a side vessel of the vasculature so that blood flow can enter the side vessel.

The conventional procedure to treat branch vessels utilizes a balloon expandable covered stent which is deployed through the side arm of the stent graft to connect the side vessels to a bifurcated stent graft. The limitation of a delivery system for such balloon expandable covered stents is normally 7 to 8 French which makes the design of the stent graft deployment system challenging. A further challenge is then providing a sufficient attachment between the branch vessel stent graft and the side arm of the main graft since endoleaks can occur and these are of significant concern.

SUMMARY OF THE INVENTION

It is the object of this invention to provide an alternative branch vessel stent graft which will make the process of deployment of a graft into a branch vessel more straightforward or at least to provide the physician with a useful alternative.

Throughout this specification the term distal with respect to a portion of the aorta, a deployment device or a prosthesis is the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

In one form therefore the invention is said to reside in a stent graft comprising a tubular body of a biocompatible material with a main lumen therethrough, a side arm extending from the tubular body with a side arm lumen therethrough and being fastened to the tubular body, the side arm having a distal end remote from its connection to the tubular body, the main lumen being in fluid communication with the side arm lumen and a tubular extension piece sealingly joined to the distal end of the side arm and extending therefrom.

Preferably the tubular body and the side arm comprise a biocompatible woven or non-woven material selected from the group comprising Dacron and expanded PTFE and the extension piece comprises an elastomeric biocompatible material such as Thoralon™.

Preferably the extension piece is tucked back into the side arm during deployment of the stent graft into a body lumen.

Preferably the extension piece is unstented. The extension piece may comprise, however, a longitudinally extending resilient reinforcement. The longitudinally extending resilient reinforcement may be a ribbon or wire formed from nitinol. The longitudinally extending resilient reinforcement is preferably embedded in the extension piece.

There can also be placed gold markers embedded in the extension piece to assist with visualisation using radiographic techniques during deployment.

The unstented extension piece is supported after deployment by a separately deployed self expanding stent assembly or by a separately deployed balloon expandable stent assembly. The separately deployed self expanding stent assembly or a separately deployed balloon expandable stent assembly may have at least one radiopaque marker to assist with visualisation using radiographic techniques during deployment.

Preferably the tubular body comprise a plurality of self expanding stents and the side arm is stitched to the tubular body. The extension piece is preferably sealingly joined to the side arm by being adhered thereto. Alternatively the extension piece is stitched to the side arm using a biocompatible suture material.

Where the extension piece comprises Thoralon™ it may be sealingly joined to the side arm by being adhered thereto by the use of a Thoralon™ solution as an adhesive.

In a further form the invention comprises a stent graft comprising a tubular body of a biocompatible material with a main lumen therethrough, a side arm extending from the tubular body with a side arm lumen therethrough and being fastened to the tubular body, the side arm having a distal end remote from its connection to the tubular body, the main lumen being in fluid communication with the side arm lumen, a tubular extension piece sealingly joined to the distal end of the side arm and extending therefrom, the extension piece including a longitudinally extending resilient reinforcement embedded therein wherein the extension piece is tucked back into the side arm during deployment of the stent graft into a body lumen.

Preferably the longitudinally extending resilient reinforcement comprised a ribbon formed from a shape memory metal such as nitinol.

In a further form the invention comprises a stent graft comprising a tubular body of a biocompatible material with a main lumen therethrough an a tubular extension piece sealingly joined to the tubular body and extending therefrom, the tubular extension piece comprising an unstented elastomeric biocompatible material and wherein the extension piece tucked back into the tubular body during deployment of the stent graft into a body lumen and extendable therefrom during deployment of the stent graft.

In one embodiment the tubular body is bifurcated and the extension piece comprises a leg extending from a bifurcation in the tubular body.

It will be seen that by this invention the stent for the extension piece is deployed in a separate stage than the deployment of the actual graft for the side arm and therefore makes it easier to use any bare stent such as a self expanding or balloon expandable stent for the stent stage. Such a separately deployed bare stent is considerably smaller in diameter than a covered balloon expandable stent for instance and therefore can be more easily deployed using existing technologies. The graft portion of the side branch is attached securely to the main side arm stent graft and loaded as an integral part. After the stent graft is implanted a bare stent can then subsequently be deployed to keep the branch vessel graft open and attached to the vasculature.

This arrangement has two significant advantages. First of all there can be a lower system delivery profile for the stent for the side arm.

A second advantage is that affective sealing can be obtained because the extension piece for the side arm is effectively sealed to the extension piece during manufacture of the stent graft.

BRIEF DESCRIPTION OF THE DRAWING

This then generally describes the invention but to assist with understanding reference will now be made to the accompanying drawings which show preferred embodiments of the invention.

In the drawings:

FIG. 1 shows a first view of a side branch stent graft with an extension piece according to one embodiment of the present invention;

FIG. 2 shows the embodiment shown in FIG. 1 with the extension piece folded back into the side arm for initial deployment;

FIG. 3 shows the side arm stent graft and extension piece of FIG. 1 after deployment and placement of a bare self expanding stent deployed through the extension piece;

FIG. 4 shows a detail of the side arm of FIG. 2 particularly showing the folded back nature of the extension piece and the radio opaque marker;

DETAILED DESCRIPTION

Figure 5:
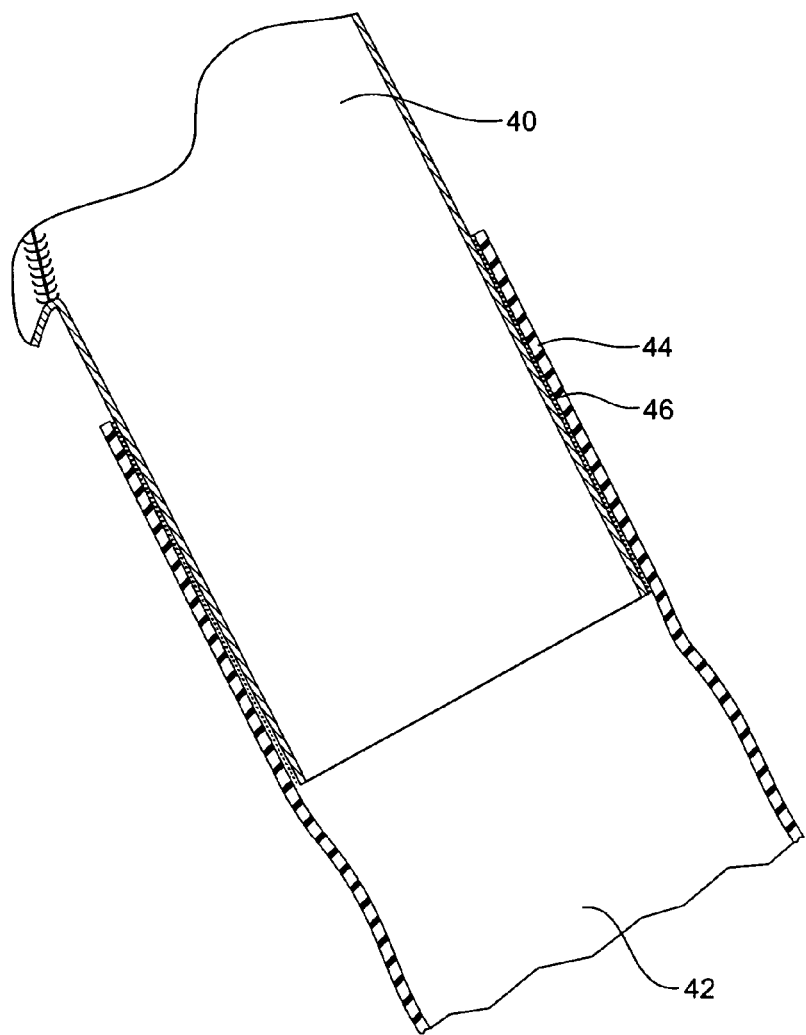
FIG. 5 shows detail of an alternative embodiment of stent graft according to the invention in which the extension piece includes a reinforcing ribbon.

Now looking more closely at the first embodiment of the invention shown in FIGS. 1, 2, and 4 it will be seen that the stent graft 10 according to the present invention comprises a tubular body 12 of a biocompatible graft material such as Dacron supported by a plurality of self expanding zigzag Gianturco stents 14. At least the self expanding stent 16 at the distal end 18 of the stent graft 10 is internal and the other stents are preferably external. A side arm 20 is stitched into the main body by stitching 22 and extends away from the body at an angle towards the distal end of the stent graft. The side arm is formed from a biocompatible graft material such as Dacron. U.S. Provisional Patent Application Ser. No. 60/611,744, filed Sep. 21, 2004, U.S. patent application Ser. No. 11/231,621, filed Sep. 21, 2005, and Published on May 4, 2006, as U.S. Patent Application Publication No. US-2006/0095118-A1, and PCT Patent Publication No. WO 06/034276 entitled "Side Branch Stent Graft" disclose methods of joining the side arm to the tubular body of the stent graft. This feature and other features disclosed in U.S. Provisional Patent Application Ser. No. 60/611,744, filed Sep. 21, 2004, U.S. patent application Ser. No. 11/231,621, filed Sep. 21, 2005, and Published on May 4, 2006, as U.S. Patent Application Publication No. US-2006/0095118-A1, and PCT Patent Publication No. WO 06/034276 could be used with the present invention and the disclosure of U.S. Provisional Patent Application Ser. No. 60/611,744, filed Sep. 21, 2004, U.S. patent application Ser. No. 11/231,621, filed Sep. 21, 2005, and Published on May 4, 2006, as U.S. Patent Application Publication No. US-2006/0095118-A1, and PCT Patent Publication No. WO 06/034276 is herewith incorporated in its entirety into this specification. Other forms of connection of the side arm to the tubular body as well as side arms that are integral with the tubular body are within the scope of the invention.

An extension piece 24 extends from a side arm 20 with an overlapped portion 26. The extension piece 24 is formed from Thoralon™ which is a polyurethane multi-polymer comprising a high flex life elastomer base with a surface modifying agent comprising siloxane which is manufactured by Thorotec Corporation (Pleasanton, Calif. USA). This material is substantially transparent and hence the distal end 27 of the side arm 20 can be seen through it.

The extension piece 24 can be adhered to the side arm 20 in the overlap region by use of a Thoralon™ solution. One method by which a Thoralon tube may be adhered to the biocompatible graft material side arm 20 is as follows. The overlapping portion 26 of the side arm is first soaked with low concentration Thoralon solution and then it is dried. The tubular Thoralon graft is then adhered onto the overlapping portion 26 by using a Thoralon solution and the solution is cured.

A first advantage of using Thoralon™ is that even after it is compressed into a small size for deployment it is resilient and can return to its original shape after deployment. This makes it possible to deploy the extension piece into a vessel.

A further advantage is that the Thoralon™ polymer is particularly hemocompatible because of the siloxane continually migrates to the blood-contacting surfaces to inhibit the attachment of proteins such as fibrin thereto.

FIG. 2 and FIG. 4 show the arrangement of the extension piece during deployment. It will be seen that the extension piece 24 is folded back inside itself and inside the side arm 20 but with its distal end 30 adjacent the distal 27 of the side arm 20. In FIG. 4 in particular it can be seen also that there is a radiopaque marker 28 embedded into the Thoralon™ extension piece 24 to assist with visualisation during deployment.

FIG. 3 shows the side arm stent graft and extension piece of FIG. 1 after deployment and placement of a bare self expanding stent deployed through the extension piece. A bare stent 32 has been deployed partly within the side arm 20 and partly within the extension piece 24 and just extending out of the distal end 30 of the extension piece 24. The bare stent 32 has a radiopaque marker 34 mounted into its distal end 35 to assist with visualisation and accurate placement during deployment. The bare stent 32 can be a self expanding stent such as a Zilver™ stent (Cook, Bloomington, Ind. USA) or a balloon expandable stent carried in and deployed on a balloon catheter. A deployment device or introducer for such a bare stent may have a diameter of 7 French which is compatible with existing delivery systems for stent grafts. It will be noted from FIG. 3 that the radiopaque marker 28 embedded into the Thoralon™ extension piece 24 is now some distance from the side arm 20 so that the physician is able to determine by radiography whether successful extension of the extension piece has occurred.

FIG. 5 shows detail of an alternative embodiment of side arm stent graft with extension piece. In this embodiment the side arm 40 of a stent graft has an extension piece 42 fastened to it on the outside of the side arm 40. by he use of a Thoralon™ adhesive 46. One method of fastening is by adhering as discussed above. The extension piece 42 has a ribbon 44 of nitinol embedded into it and extending longitudinally along the extension piece. By this arrangement when the extension piece is extended from the position where it is retracted within the side arm as shown in FIG. 4 for instance to the extended configuration as shown in FIG. 1 for instance the nitinol ribbon assists with straightening and reinforcing the extension piece. Hence the nitinol ribbon 44 provides a resilient reinforcement for the extension piece 42. Alternatively the reinforcement may be a resilient wire. The wire or ribbon may alternatively be formed from resilient stainless steel.

Figures 6, 7:
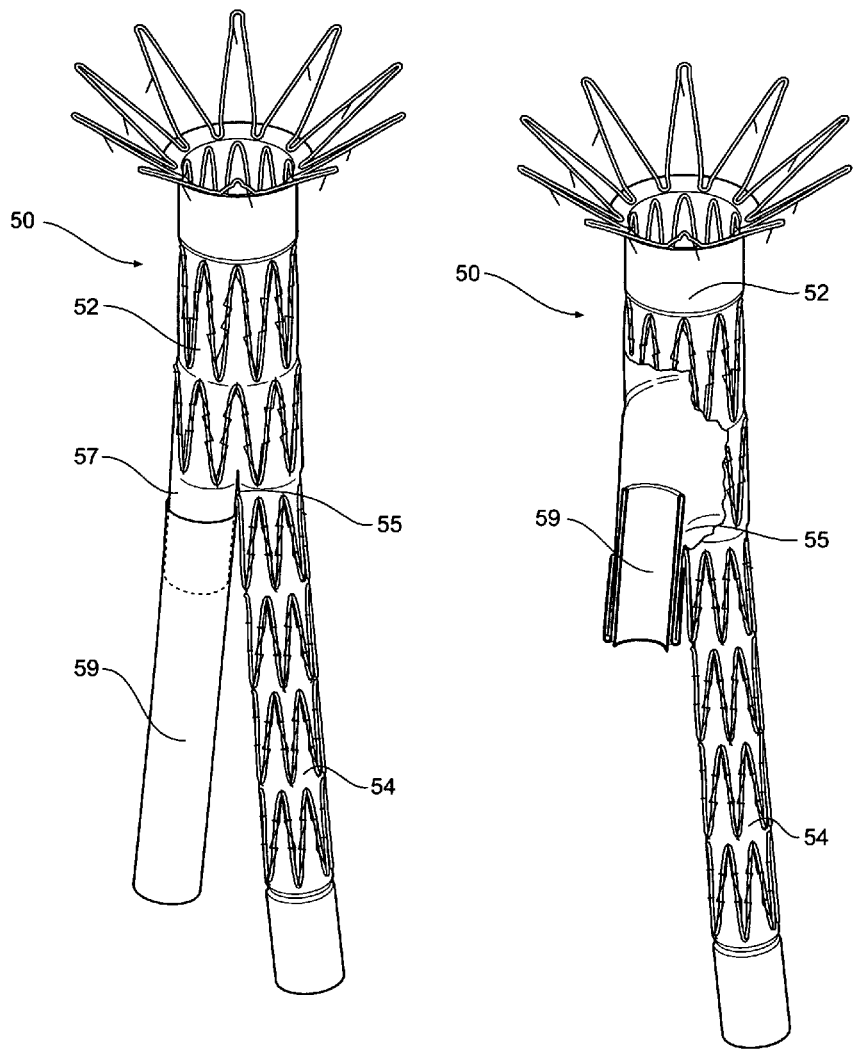
FIG. 6 shows an alternative embodiment of stent graft according to the invention including an extension piece according to the present invention.
FIG. 7 shows the embodiment of FIG. 6 with the extension piece retracted for deployment.

FIG. 6 shows an alternative embodiment of stent graft according to the invention including an extension piece according to the present invention, and FIG. 7 shows the embodiment of FIG. 6 with the stent graft part cutaway to show the extension piece retracted into the stent graft for deployment.

In FIG. 6 there is illustrated a bifurcated stent graft suitable for deployment into an aorta to span an aneurysm which incorporates the aortic bifurcation. The stent graft 50 has a tubular body 52 and a first leg 54 extending from a bifurcation 55. A second leg extending from the bifurcation 55 is comprised partly as a leg 57 being a continuation of the tubular body 52 and then an extension piece 59 comprised from a elastomeric material such as expanded PTFE or Thoralon. The extension piece 59 is fastened to the leg 57 by adhering as discussed above or any other fastening technique such as stitching.

FIG. 7 shows the embodiment of FIG. 6 but part of the tubular body 52 is cutaway to show the extension piece 59 folded back into the main tubular body for deployment.

Upon deployment of the stent graft according to this embodiment the stent graft is deployed so that the tubular body 52 is in the aorta and the leg 54 extends down one of the iliac arteries and then the extension piece 59 can then be pushed out to extend down the contra-lateral iliac artery and then a bare stent such as a self expanding or balloon expandable stent can be deployed into the contra-lateral iliac artery to seal the extension piece against the wall of the contra-lateral iliac artery. The extension piece may include a reinforcing ribbon or wire of nitinol or stainless steel and may include one or more radiopaque markers.

Figure 8:
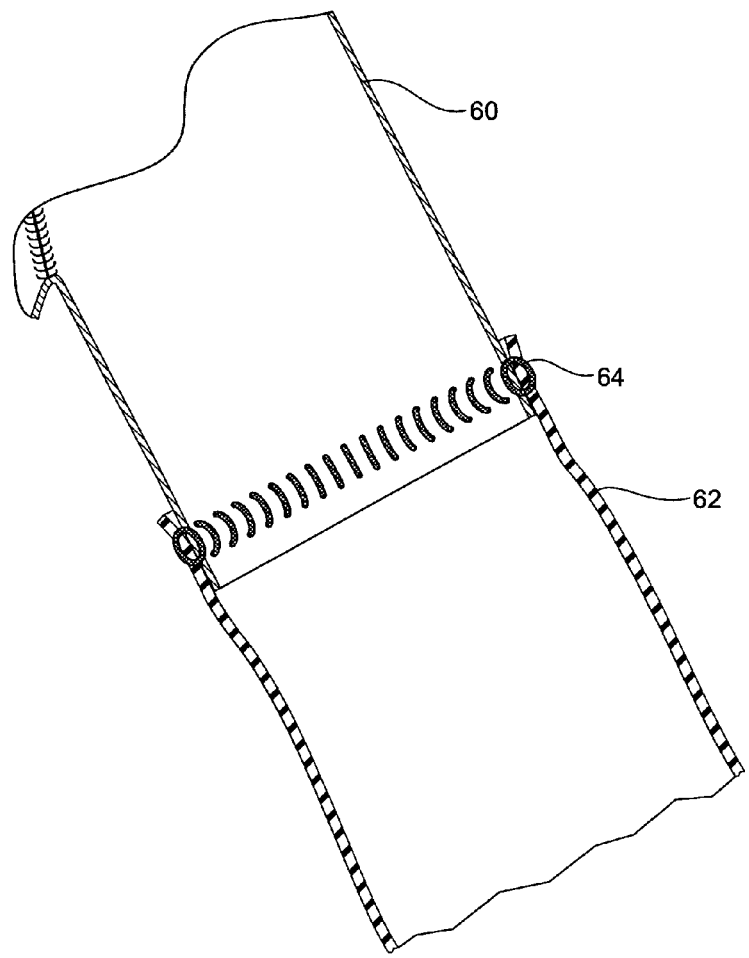
FIG. 8 shows an alternative method of joining the extension piece to the side arm according to the present invention.

FIG. 8 shows an alternative method of joining the extension piece to the side arm according to the present invention. In this embodiment the side arm 60 of a stent graft has an extension piece 62 of a biocompatible elastomeric material stitched to it by stitching 64. The stitching provides a fluid type seal between the extension piece and the side arm which reduce the chance of endoleaks after deployment of the stent graft into the vasculature of a patient.

Throughout this specification various indications have been given as to the scope of this invention but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

What is claimed is:

1. A stent graft comprising a tubular body of a woven biocompatible material with a main lumen therethrough, a side arm connected to and extending from the tubular body with a side arm lumen therethrough and being fastened to the tubular body, the side arm having a predelivery configuration and a post delivery configuration, the side arm comprising a woven biocompatible material, the side arm having a distal end remote from its connection to the tubular body and a distal end portion adjacent the distal end, the main lumen being in fluid communication with the side arm lumen, a tubular extension piece having a proximal end and a distal end, and extending from the distal end of the side arm and overlapping an outer surface of the side arm at the distal end portion in a sealing relationship and forming an overlapping region, wherein the overlapping region of the tubular extension piece is adhesively fastened to the distal end of the side arm, the tubular extension piece comprising a polyurethane multi-polymer material, the distal end of the tubular extension piece folded back inside the tubular extension piece and being tucked back into the side arm in the predelivery configuration and extending entirely outside of the side arm in the post delivery configuration, the tubular extension piece further comprising a longitudinally extending resilient reinforcement embedded therein, the longitudinally extending resilient reinforcement comprising a resilient wire ribbon extending along the length of the tubular extension piece and along a portion of the overlapping region, and the extension piece comprising a non-woven elastomeric biocompatible material, and at least one radiopaque marker separate from the resilient reinforcement embedded into the distal end of the tubular extension piece.

2. A stent graft as in claim 1 wherein the proximal end of the tubular extension piece is sealingly joined to and integral with the side arm by being adhered thereto.

3. A stent graft as in claim 1 wherein the proximal end of the tubular extension piece is sealingly joined to and integral with the side arm by being adhered thereto by the use of a polyurethane multi-polymer material solution.

4. A stent graft as in claim 1 wherein the proximal end of the tubular extension piece is joined to and integral with the side arm by being stitched thereto.

* * * * *